United States Patent
Koehler et al.

(10) Patent No.: US 10,420,519 B2
(45) Date of Patent: Sep. 24, 2019

(54) COMPUTED TOMOGRAPHY SYSTEM

(71) Applicant: KONINKLIJKE PHILIPS N.V., Eindhoven (NL)

(72) Inventors: Thomas Koehler, Norderstedt (DE); Roland Proksa, Neu Wulmstorf (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 302 days.

(21) Appl. No.: 15/523,690

(22) PCT Filed: Nov. 4, 2015

(86) PCT No.: PCT/EP2015/075650
§ 371 (c)(1),
(2) Date: May 2, 2017

(87) PCT Pub. No.: WO2016/071374
PCT Pub. Date: May 12, 2016

(65) Prior Publication Data
US 2017/0332982 A1    Nov. 23, 2017

(30) Foreign Application Priority Data

Nov. 6, 2014 (EP) ..................... 14192039

(51) Int. Cl.
G06K 9/00 (2006.01)
A61B 6/03 (2006.01)
(Continued)

(52) U.S. Cl.
CPC ............ A61B 6/032 (2013.01); A61B 6/027 (2013.01); A61B 6/4241 (2013.01); A61B 6/481 (2013.01);
(Continued)

(58) Field of Classification Search
None
See application file for complete search history.

(56) References Cited

U.S. PATENT DOCUMENTS

| 4,662,379 A | 5/1987 | Macovski |
| 6,650,724 B2 | 11/2003 | Strobel |

(Continued)

FOREIGN PATENT DOCUMENTS

| WO | 2013/186661 | 12/2013 |
| WO | 2015/189730 | 12/2015 |

OTHER PUBLICATIONS

Llopart, X., et al., "First test measurements of a 64k pixel readout chip working in a single photon counting mode", Nucl. Inst. and Meth. A, 509 (1-3): 157-163, 2003.
(Continued)

Primary Examiner — Soo Jin Park

(57) ABSTRACT

The invention relates to a computed tomography system (30). Several sets of spectral projections, which correspond to different positions of a radiation source (2) along a rotation axis (R), are decomposed into first projections being indicative of a contrast agent and second projections being not indicative of the contrast agent. An image is generated by a) determining for each first projection a contrast value being indicative of a total amount of contrast agent and scaling the first projections such that for different first projections of a same set the same contrast value is determined, and reconstructing an image based on the scaled first projections, and/or b) reconstructing for the different sets first images, scaling the first images such that they have a same intensity in overlap regions and combining the scaled first images. Thus, different contrast agent amounts can be balanced, thereby allowing for an improved image quality.

14 Claims, 3 Drawing Sheets

(51) Int. Cl.
*A61B 6/02* (2006.01)
*A61B 6/00* (2006.01)

(52) U.S. Cl.
CPC ............ *A61B 6/482* (2013.01); *A61B 6/5205* (2013.01); *A61B 6/5241* (2013.01)

(56) References Cited

U.S. PATENT DOCUMENTS

| | | |
|---|---|---|
| 7,236,559 B2 | 6/2007 | Jha |
| 7,986,822 B2 | 7/2011 | Hall |
| 8,055,050 B2 | 11/2011 | Roessl |
| 9,747,704 B2 * | 8/2017 | Taguchi ................ G06T 11/005 |
| 9,943,279 B2 * | 4/2018 | Fan ........................ A61B 6/482 |
| 2009/0028409 A1 | 1/2009 | Tsukagoshi |
| 2010/0166281 A1 | 7/2010 | Buerger |
| 2011/0026790 A1 | 2/2011 | Kargar |
| 2013/0261441 A1 | 10/2013 | Das |

OTHER PUBLICATIONS

Llopart, X., et al., "Medipix2: A 64-k pixel readout chip with 55 μm square elements working in a single photon counting mode", IEEE Trans. Nucl. Sci. 49(5): 2279-2283, 2002.

* cited by examiner

COMPUTED TOMOGRAPHY SYSTEM

CROSS REFERENCE TO RELATED APPLICATIONS

This application is the U.S. National Phase application under 35 U.S.C. § 371 of International Application No. PCT/EP2015/075650, filed Nov. 4, 2015, published as WO 2016/071374 on May 12, 2016, which claims the benefit of European Patent Application Number 14192039.7 filed Nov. 6, 2014. These applications are hereby incorporated by reference herein.

FIELD OF THE INVENTION

The invention relates to a computed tomography system, method and computer program for generating an image of a subject comprising a contrast agent.

BACKGROUND OF THE INVENTION

A computed tomography system comprises a radiation source emitting radiation traversing a subject to be imaged and a detector for generating detection values depending on the radiation having traversed the subject. The detection values are generated, while the radiation source and the subject move relative to each other, for instance, while the radiation source rotates around the subject. The computed tomography system further comprises a reconstruction unit for reconstructing an image based on the generated detection values.

If a contrast agent has been injected into the subject, the distribution of the contrast agent within the subject changes with time. Detection values, which have been generated at different times, relate therefore to different concentrations of the contrast agent within the subject, which can lead to image artifacts in the finally reconstructed image.

US20113/0261441A1 discloses determining an amount of a contrast agent in an image from simulated monochromatic contrast-enhanced images, each obtained at a different energy.

SUMMARY OF THE INVENTION

It is an object of the present invention to provide a computed tomography system, method and computer program for generating an image of a subject comprising a contrast agent, wherein the quality of the image can be improved.

In a first aspect of the present invention a computed tomography system for generating an image of a subject comprising a contrast agent is presented, wherein the computed tomography system comprises:
  a projections providing unit for providing several sets of spectral projections of the subject, wherein the several sets of projections have been acquired by detecting radiation, which has been emitted by a radiation source and which has traversed the subject, on a detection surface of a detector, while the radiation source and the subject have rotated relative to each other around a rotation axis, wherein different sets of spectral projections correspond to different positions of the radiation source along the rotation axis,
  a decomposition unit for decomposing the spectral projections into first projections being indicative of the contrast agent within the subject and second projections not being indicative of the contrast agent within the subject,
  an image generation unit for generating the image by a) determining for each first projection a contrast value being indicative of a total amount of contrast agent based on projection values of the respective first projection acquired within a respective region of interest on the detection surface and scaling the first projections such that for different first projections of a same set the same contrast value is determined, and reconstructing the image based on the scaled first projections, and/or b) reconstructing for the different sets first images based on the respective first projections, wherein the first images partly overlap in overlap regions, scaling the first images such that overlapping first images have a same intensity in the respective overlap region with respect to a predefined similarity measure and combining the scaled first images for generating the image.

By the scaling procedure, which may be performed in the projection domain and/or in the image domain, different amounts of the contrast agent, which may be present at different times, can be balanced, which allows for an improved quality of the finally reconstructed image.

The projections providing unit can be a storing unit, in which the projections are stored already and from which the projections can be retrieved for providing them. The projections providing unit can also be a receiving unit for receiving the projections from a projections acquisition unit and for providing the received projections. The projections providing unit can also be the projections acquisition unit itself. The projections acquisition unit can comprise the radiation source for emitting radiation traversing the subject and the detector with the detection surface, on which the radiation is detected, after having traversed the subject, wherein the spectral projections are formed by spectral detection values generated by the detector.

In an embodiment the radiation source is a polychromatic radiation source and the detector is adapted to spectrally detect the radiation after having traversed the subject. However, the spectral projections can also be acquired in another way. For example, at least two monochromatic radiation sources may be used, wherein each radiation source may emit radiation having another energy. In this case for each radiation source a corresponding non-spectral detector may be used for generating the projections. In general, known techniques can be used for providing the spectral projections like dual layer and spectral photon counting detection techniques and/or dual source and tube voltage switching techniques.

The radiation source and the subject rotate relative to each other around a rotation axis, i.e., for instance, the subject may be arranged along the rotation axis and the radiation source may rotate around the subject. The acquisition of the projections is preferentially a step-and-shoot acquisition, wherein at different positions along a longitudinal axis of the subject, which substantially coincides with the rotation axis of the rotational movement of the radiation source relative to the subject, the radiation source moves along a circular trajectory around the subject.

The decomposition unit is adapted to decompose the spectral projections into two or more components, wherein one of these components forming the first projections is indicative of the contrast agent within the subject and the one or more other components are not indicative of the contrast agent within the subject. The decomposition unit can be adapted to decompose the spectral projections into only first and second projections, wherein the first projections are indicative of the contrast agent within the subject and the second projections are not indicative of the contrast agent within the subject, or the decomposition unit can be adapted to decompose the spectral projections into first projections, second projections, third projections and optionally further projections, wherein the first projections are indicative of the contrast agent within the subject and the other projections are not indicative of the contrast agent within the subject. The decomposed projections, which are not indicative of the contrast agent within the subject, may be indicative of different other materials within the subject and/or different physical effects. For instance, the decomposed projections, which are not indicative of the contrast agent, can be indicative of, for instance, bone and soft tissue of the subject and/or of the photoelectric effect and the Compton effect.

The image generation unit may be adapted to reconstruct the image also based on the second projections, i.e., in particular, the image generation unit may be adapted to generate the image by determining for each first projection a contrast value being indicative of a total amount of contrast agent based on projection values of the respective first projection acquired within a respective region of interest on the detection surface and scaling the first projections such that for different first projections of a same set the same contrast value is achieved, and reconstructing an image based on the scaled first projections and the second projections. Moreover, the image generation unit may be adapted to reconstruct second images based on the respective second projections and to combine the scaled first images with the second images for generating the image.

The subject is preferentially a living being and the provided sets of spectral projections are preferentially cardiac gated, especially prospective cardiac gated. For performing the prospective cardiac gated acquisition of the spectral projections an electrocardiography signal generated by an electrocardiography unit connected to the subject may be used. By using cardiac gated spectral projections, image artifacts, which may be caused by a cardiac movement, may be reduced, thereby further improving the quality of the reconstructed image. Moreover, by performing a prospective cardiac acquisition of the spectral projections, the radiation dose applied to the subject can be significantly reduced.

The predefined similarity measure preferentially depends on an average of the intensity values of the respective first image in the respective overlap region. The average may be, for instance, the arithmetic mean or the median or another average. Using this average as a similarity measure leads to an improved image quality, wherein the average of the intensity values of the respective first image in the respective overlap region can be calculated with low computational effort. First images may be regarded as having a same intensity in an overlap region, if a difference between a) a similarity value obtained by applying the similarity measure to the intensities of one of the first images in the overlap region and b) a similarity value obtained by applying the similarity measure to the intensities of the other of the first images in the overlap region is smaller than a predefined threshold. The predefined threshold may be predetermined by calibration or in another way such that the image quality is improved. In an embodiment first images may be regarded as having a same intensity in an overlap region, if a difference between a) a similarity value obtained by applying the similarity measure to the intensities of one of the first images in the overlap region and b) a similarity value obtained by applying the similarity measure to the intensities of the other of the first images in the overlap region are equal.

In an embodiment the region of interest on the detection surface is the entire detection surface. Thus, the image generation unit may be adapted to scale the first projections such that the contrast value being indicative of the total amount of the contrast agent, which has been determined based on the respective entire first projection, is the same for each first projection of a same set. Since the respective entire first projection is used for determining the contrast value, i.e. since a selection of certain projection values for being used for determining the contrast value is not performed, the contrast value is indicative of the total amount of the contrast agent in the entire traversed part of the subject and the calculation of the contrast value and the corresponding scaling of the first projections can be performed with relatively low computational effort.

In another embodiment the respective region of interest on the detection surface corresponds to a virtual projection of a predefined object of interest within the subject on the detection surface. Preferentially, the projections providing unit is adapted to provide the respective acquisition geometry used for acquiring the respective projection, wherein the image generation unit is adapted to provide an object of interest image showing the object of interest within the subject and to determine the respective region of interest on the detection surface by virtually projecting the object of interest onto the detection surface under consideration of the provided respective acquisition geometry and the provided object of interest image. For instance, if the object of interest is the heart, the region of interest on the detection surface may correspond to a virtual projection of the heart onto the detection surface. Thus, for determining the contrast value being indicative of the total amount of the contrast agent based on projection values of a respective first projection only projection values may be used, which are within the region of interest on the detection surface, wherein the region of interest corresponds to the virtual projection of the predefined object of interest onto the detection surface. The contrast value may therefore be indicative of the total amount of contrast agent in the object of interest only. This can lead to an improved scaling regarding the object of interest and hence finally to an improved quality of an image of the object of interest.

The image generation unit may be adapted to parallel rebin the first projections and optionally also the second projections before using the first projections and optionally also the second projections for reconstruction, especially before determining contrast values for the first projections. The parallel rebinning can lead to further reduced computational efforts for generating the image.

In a further aspect of the present invention a computed tomography method for generating an image of a subject comprising a contrast agent is presented, wherein the computed tomography method comprises:

providing several sets of spectral projections of the subject by a projections providing unit, wherein the several sets of projections have been acquired by detecting radiation, which has been emitted by a radiation source and which has traversed the subject, on a detection surface of a detector, while the radiation source and the subject have rotated relative to each other around a rotation axis, wherein different sets of spectral projections correspond to different positions of the radiation source along the rotation axis, decomposing the spectral projections into first projections being indicative of the contrast agent within the subject and second projections being not indicative of the contrast agent within the subject by a decomposition unit, generating the image by an image generation unit by a) determining for each first projection a contrast value being indicative of a total amount of contrast agent based on projection values of the respective first projection acquired within a respective region of interest on the detection surface, scaling the first projections such that for different first projections of a same set the same contrast value is determined and reconstructing the image based on scaled first projections, and/or b) reconstructing for the different sets first images based on the respective first projections, wherein the first images partly overlap in overlap regions, scaling the first images such that overlapping first images have a same intensity in the respective overlap region with respect to a predefined similarity measure and combining the scaled first images for generating the image.

In another aspect of the present invention a computer program for generating an image of a subject comprising a contrast agent is presented, wherein the computer program comprises program code means for causing a computed tomography system as defined in claim 1 to carry out the steps of the computed tomography method as defined in claim 11, when the computer program is run on a computer controlling the computed tomography system.

It shall be understood that the computed tomography system of claim 1, the computed tomography method of claim 11, and the computer program of claim 12 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
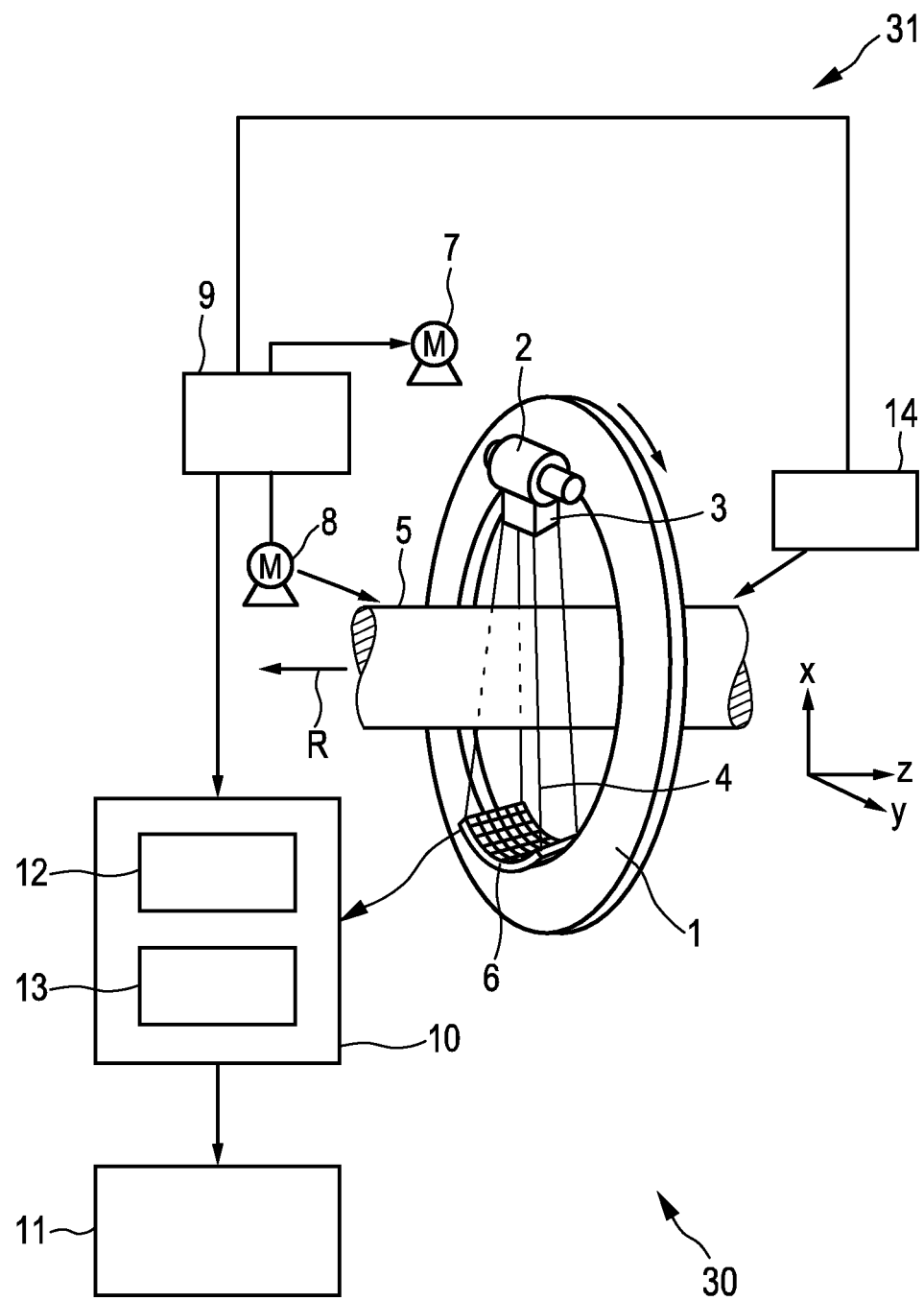
FIG. 1 shows schematically and exemplarily an embodiment of a computed tomography system for generating an image of a subject comprising a contrast agent.

FIG. 1 shows schematically and exemplarily a computed tomography system 30 for generating an image of a subject. The computed tomography system 30 comprises a projections acquisition unit 31 for acquiring several sets of spectral projections of the subject, a processing unit 10 for processing the provided sets of spectral projections, especially for generating an image, and a display 11 for showing the generated image. In this embodiment the subject is a person and the projections acquisition unit 31 is adapted to perform a prospective cardiac gated acquisition of the spectral projections.

The projections acquisition unit 31 includes a gantry 1 which is capable of rotation around a rotation axis R which extends parallel to a z direction. A polychromatic radiation source 2, which is, in this embodiment, an x-ray tube, is mounted on the gantry 1. The radiation source 2 is provided with the collimator 3 for forming, in this embodiment, a conical radiation beam 4 from the radiation generated by the radiation source 2. The radiation 4 traverses the subject (not shown), in which a contrast agent has been injected, in an examination zone 5, which is, in this embodiment, cylindrical. After having traversed the examination zone 5 the radiation beam 4 impinges on an energy-resolving detector 6 comprising a two-dimensional detection surface. The detector 6 is mounted on the gantry 1. In another embodiment the collimator 3 can be adapted for forming another beam shape, in particular, a fan beam, and the detector 6 can comprise a detection surface which is shaped corresponding to the other beam shape, in particular to the fan beam.

The energy-resolving detector works, for example, on the principle of counting the incident photons and of outputting spectral detection values that show the number of photons per energy in a certain energy range. Such an energy-resolving detector is, for example, described in the articles Llopart, X., et al., "First test measurements of a 64 k pixel readout chip working in a single photon counting mode", Nucl. Inst. and Meth. A, 509 (1-3): 157-163, 2003 and in Llopart, X., et al., "Medipix2: A 64-k pixel readout chip with 55 µm square elements working in a single photon counting mode", IEEE Trans. Nucl. Sci. 49(5): 2279-2283, 2002, which are herewith incorporated by reference.

The projections acquisition unit 31 comprises two motors 7, 8. The gantry is driven at a preferably constant but adjustable angular speed by the motor 7. The motor 8 is provided for displacing the subject who is arranged on a subject table in the examination zone 5 parallel to the direction of the rotation axis R or the z-axis. These motors 7, 8 are controlled by control unit 9 such that a step-and-shoot acquisition is performed, i.e. at different positions along the rotation axis R or the z-axis spectral projections are acquired, while the radiation source 2 is moved around the subject along a circular trajectory. The spectral projections acquired at a certain position along the rotation axis R or the z-axis are regarded as belonging to a same set of spectral projections.

During the movement of the radiation source 2 around the subject along a circular trajectory at a respective position along the rotation axis R or the z-axis the detector 6 generates energy-dependent detection values depending on the radiation impinging on the detection surface of the detector 6, wherein energy-dependent detection values acquired at a same time form a spectral projection.

In this embodiment the projections acquisition unit 31 further comprises an electrocardiography unit 14 for generating an electrocardiography signal of the subject. This electrocardiography signal is provided to the control unit 9 in order to allow the control unit 9 to control the acquisition of the projections such that the acquisition is prospectively cardiac gated. In particular, spectral projections are acquired only at a certain cardiac phase indicated by the electrocardiography signal. This certain cardiac phase is preferentially a quiet phase in which there are no large movements of the heart.

The spectral projections are transmitted to the processing unit 10, which may also be controlled by the control unit 9, via a wired or wireless data connection. The processing unit 10 comprises a decomposition unit 12 for decomposing the spectral projections into first projections being indicative of the contrast agent, which has been injected into the subject, and second and third projections, which are not indicative of the contrast agent within the subject. The decomposition unit 12 is preferentially adapted to apply a component decomposition technique to the spectral projections for determining K-edge attenuation values being first component attenuation values, which are indicative of an attenuation caused by a K-edge of the contrast agent and which form the first projections, and additional component attenuation values, which are indicative of an attenuation caused by additional components of the subject and which form, in this embodiment, second and third projections, by using the energy dependency of the detection values forming the spectral projections acquired by the projections acquisition unit 31. An attenuation value corresponds to a line integral of absorption coefficients along a ray having caused the respective detection value.

In this embodiment the decomposition unit 12 is adapted to apply a physical effect decomposition technique to the detection values of the spectral projections acquired by the projections acquisition unit 31. However, the decomposition unit 12 can also be adapted to apply a base material decomposition technique to the detection values. In particular, the decomposition unit 12 is adapted to apply a component decomposition technique to the detection values for determining K-edge attenuation values being first component attenuation values, which are indicative of an attenuation caused by the contrast agent and which form the first projections, and additional component attenuation values being second component attenuation values, which are indicative of an attenuation caused by a second component and which form second projections, and third component attenuation values, which are indicative of an attenuation caused by a third component and which form third projections, from the energy dependency of the detection values. The second component is a photoelectric effect component of the examination zone and the third component is a Compton effect component of the examination zone. Alternatively, the second and third component may be other components like water and bone, tin and water, or tin and Delrin components. For determining the K-edge attenuation values and the additional component attenuation values the decomposition unit 12 is adapted to solve a system of equations for the energy-dependent detection values, wherein a model is used for the detection values describing an energy-dependent detection value as a combination of the K-edge effect of the contrast agent, the photoelectric effect and the Compton effect, each effect contributing with a corresponding attenuation to the respective energy-dependent detection value. This system of equations can be, for example, defined as follows:

$$I_b^n = \int S_b(E)\phi(E)e^{-\Sigma_{m\in M} f_m(E) A_m^n} dE, \qquad (1)$$

wherein $I_b^n$ is the respective detection value defined by a measurement parameter n and an energy bin b, wherein the measurement parameter n is defined by the respective detection element of the detector 6 and the acquisition time. The spectral sensitivity within the energy bin b is denoted by $S_b(E)$, the radiation flux from the radiation source 2 is denoted by $\phi(E)$, the different effects like the K-edge effect, the photoelectric effect and the Compton effect, or in other words different components or different contributions, are denoted by m from the set of effects M, the energy-dependent function of the respective effect m, or in other words the energy-dependent attenuation of the respective component m, is denoted by $f_m(E)$, and $A_m^n$ denotes the attenuation values, i.e. the attenuation line integrals, of the respective effect m contributing to the detection value defined by the measurement parameter n.

In this embodiment the number of energy bins is at least three such that the system of equations can be solved with known numerical methods, wherein the quantities $S_b(E)$, $\phi(E)$ and $f_m(E)$ are known and the result of solving the system of equations are the attenuation values $A_C^n$, $A_P^n$ and $A_K^n$ for the Compton effect, the photoelectric effect and the K-edge effect, respectively. The spectral sensitivity $S_b(E)$ and the radiation flux from the radiation source $\phi(E)$ are characteristics of the detection apparatus and are known from, for example, corresponding measurements of the detection apparatus. The energy-dependent functions $f_m(E)$ of the modeled effects are also known from measurements and/or from literature.

The processing unit 10 further comprises an image generation unit 13 for generating a computed tomography image based on the first, second, and third projections. In this embodiment the image generation unit 13 is adapted to reconstruct for each set, i.e. for each position along the rotation axis R or the z-axis, a respective first image based on the respective first projections, a respective second image based on the respective second projections and a respective third image based on the respective third projections. The spectral projections have been acquired such and the reconstruction is performed such that the first images of the different sets, i.e. the first images which correspond to the different positions along the rotation axis R or the z-axis, partially overlap in overlap regions.

For reconstructing an image based on projections the image generation unit 13 can be adapted to use known reconstruction algorithms like a filtered backprojection algorithm, an iterative reconstruction algorithm, a Radon inversion algorithm, et cetera.

The image generation unit 13 is adapted to scale the first images such that they have a same intensity in the respective overlap region with respect to a predefined similarity measure, wherein the predefined similarity measure is preferentially the average of the intensity values of the respective first image in the respective overlap region. The scaled first images are then combined with the second and third images for generating a final reconstructed image.

The image generation unit 13 can be further adapted to scale the decomposed first projections before using these projections for reconstructing an image. In particular, the image generation unit 13 can be adapted to determine for each first projection a contrast value being indicative of a total amount of contrast agent based on projection values, i.e. attenuation values, of the respective first projection acquired within a respective region of interest on the detection surface of the detection 6, wherein the first projections are scaled such that for different first projections of a same set the same contrast value is determined. The image generation unit 13 may be adapted to parallel rebin the decomposed projections, before determining the contrast value and before scaling the decomposed first projections. The image generation unit 13 can be adapted to use the scaled first projections and the second and third projections for reconstructing an image of the subject.

The image generation unit 13 can be adapted to perform either the projection scaling procedure or the image scaling procedure, or the image generation unit 13 can be adapted to firstly perform the projection scaling procedure and to then apply the image scaling procedure by using the already scaled first projections.

Figure 2:
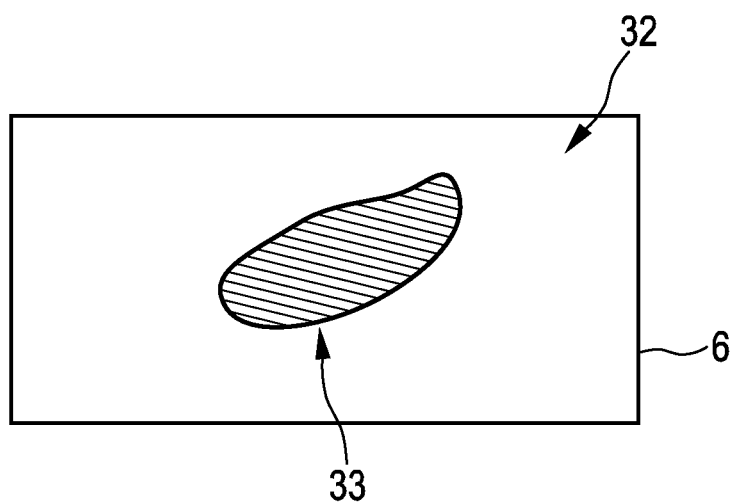
FIG. 2 shows schematically and exemplarily a detection surface of a detector of the computed tomography system.

The region of interest on the detection surface, which defines which projection values, i.e. attenuation values, of a first projection are used for determining the contrast value being indicative of the total amount of the contrast agent, can be the entire detection surface. In this case all projection values of a respective first projection are used for determining the contrast value. However, in a preferred embodiment the region of interest 33 on the detection surface 32 corresponds to a virtual projection of a predefined object of interest within the subject on the detection surface 32 as schematically and exemplarily illustrated in FIG. 2. In particular, the projections acquisition unit 31 is preferentially adapted to provide the respective acquisition geometry used for acquiring the respective projection and the image generation unit 13 is adapted to provide an object of interest image showing the object of interest within the subject and to determine the respective region of interest 33 on the detection surface 32 by virtually projecting the object of interest onto the detection surface 32 under consideration of the provided respective acquisition geometry and the provided object of interest image. For instance, if the object of interest is the heart, the image generation unit 13 can be adapted to provide an image of the heart as the object of interest image. For example, before performing the step-and-shoot acquisition procedure, a low-dose computed tomography scan can be performed, in order to provide a low-dose object of interest image showing the heart of the subject. The image generation unit 13 may be adapted to segment the heart in the object of interest image, wherein the segmented object of interest image can be used together with the known acquisition geometry, in order to determine for each position of the radiation source 2 relative to the subject a region of interest 33 on the detection surface 32 by simulating a corresponding forward projection.

For determining the contrast value being indicative of the total amount of the contrast agent based on a respective first projection, a predefined relation between a projection value, i.e. an attenuation value, and an amount of contrast agent can be used. Moreover, the contrast value may be determined based on the assumption that the projection value is proportional to the total amount of contrast agent along the corresponding ray, wherein the divergence of the rays is neglected. This assumption leads to good results, especially if a parallel rebinning is performed before determining the contrast value. In particular, since all rays, which correspond to a first projection, do not overlap, the sum of all projection values of a first projection within a respective region of interest on the detection surface can be regarded as being proportional to the total amount of contrast agent. As a contrast value this sum of all projection values can therefore be determined.

Figure 3:
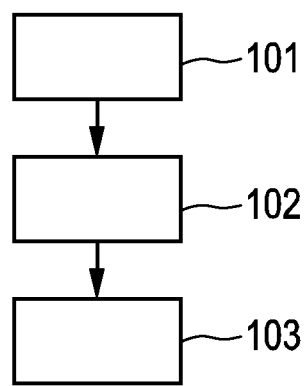
FIG. 3 shows a flowchart exemplarily illustrating an embodiment of a computed tomography method for generating an image of a subject comprising a contrast agent.

In the following an embodiment of a computed tomography method for generating an image of a subject comprising a contrast agent will exemplarily be described with reference to a flowchart shown in FIG. 3.

After the contrast agent has been injected into the subject, in step 101 the projections acquisition unit 31 acquires several sets of spectral projections of the subject in a step-and-shoot manner. The different sets of the spectral projections correspond to different positions of the radiation source along the rotation axis R and the spectral projections of a same set correspond to different positions along a circular trajectory around the subject at a same position on the rotation axis R. Preferentially, during the acquisition of the spectral projections an electrocardiography signal is provided by the electrocardiography unit 14 and the acquisition of the spectral projections is gated depending on the provided electrocardiography signal.

In step 102 the decomposition unit 12 decomposes the acquired spectral projections into first projections being indicative of the contrast agent within the subject and further projections being not indicative of the contrast agent within the subject. In particular, the spectral projections are decomposed into first projections being indicative of the contrast agent, second projections being indicative of the photoelectric effect and third projections being indicative of the Compton effect.

In step 103 the image generation unit 13 generates an image of the subject based on the decomposed projections. In particular, for each first projection a contrast value being indicative of a total amount of contrast agent may be determined based on the projection values of the respective first projection, which have been acquired within a respective region of interest 33 on the detection surface 32, wherein the first projections may be scaled such that for different first projections of a same set the same contrast value is determined. The image generation unit 13 may then reconstruct the image based on the scaled first projections and optionally also based on the second and third projections. Alternatively or in addition, the image generation unit 13 may reconstruct for the different sets first images based on the respective first projections, wherein the acquisition of the spectral projections and the reconstruction is preferentially performed such that the first images partly overlap in overlap regions. The image generation unit 13 may then scale the first images such that overlapping first images have a same intensity in the respective overlap region with respect to a predefined similarity measure. The scaled first images and optionally also second and third images, which may be reconstructed based on the second and third projections, can finally be combined, in order to provide a final image.

The projections acquisition unit is preferentially adapted to perform a step-and-shoot acquisition with prospective electrocardiographic gating, wherein the computed tomography system 31 is preferentially adapted to perform a cardiac computed tomography scan, especially for persons with regular and rather low heart rate. Generally, the temporal discontinuity between the steps could lead to strong and annoying banding artifacts in the finally reconstructed image, because between the steps the bolus of the contrast agent often washes out considerably. The computed tomography system described above with reference to FIGS. 1 and 2 is therefore adapted to exploit the possibility to separate the contrast agent from the surrounding tissue. In particular, the computed tomography system is adapted to perform j=1, . . . , N overlapping axial scans, i.e. the projections acquisition unit is adapted to acquire spectral projections at different positions along the rotation axis R or the z-axis, wherein at each position the radiation source moves along a circular trajectory around the subject for acquiring the spectral projections and wherein the distance between adjacent positions along the rotation axis R or the z-axis, at which the spectral projections are acquired, is chosen such that for each of these positions an image can be reconstructed which overlaps with an image reconstructed for a neighboring position. These spectral projections are decomposed into contrast agent projections, i.e. first projections, and other, non-contrast agent projections, which may correspond to, for instance, different materials and/or different physical effects.

The computed tomography system is further adapted to reconstruct a contrast agent only image $I_j$ for each step j of the acquisition. That means at each position along the rotation axis R or the z-axis, at which projections have been acquired, a first image is reconstructed based on the respective first projections. The signal level in these images $I_j$ is then adjusted such that a smooth transition is obtained between the steps, which results in rescaled contrast agent images $K_j$, i.e. rescaled first images. Preferentially, the different images $I_j$ overlap by a few millimeters such that the adjustment can easily be achieved by rescaling the images $I_j$ such that the same mean signal level is reached in the respective overlapping region. The computed tomography system can be further adapted to reconstruct further images based on the further, non-contrast agent projections and to combine these further images with the rescaled contrast agent images $K_j$, in order to generate a final computed tomography image. In particular, the different images can be combined to a conventional image, i.e. an image showing energy-averaged absorption values, or to a monochromatic image.

The spectral detection also facilitates a compensation of contrast agent dynamics within a step. In particular, for each axial scan the computed tomography system can perform following steps. The projections can be decomposed into contrast agent projections, i.e. first projections, and further, non-contrast-agent projections. Optionally, a region of interest on the detection surface of the detector may be masked, i.e. a region of interest may be defined on the detection surface, wherein this region of interest preferentially corresponds to a forward projection of an object of interest like the heart. Moreover, the projections may be parallel rebinned. Then, the total amount of the contrast agent in the field of view of the computed tomography system or, if a region of interest has been defined on the detection surface of the detector, in a corresponding object of interest is estimated by computing the total signal intensity of the contrast agent projection for each first projection of the respective axial scan. These first projections are then rescaled such that the same total amount of contrast agent is achieved in the field of view or in the object of interest, respectively. Finally, an image is reconstructed using the rescaled contrast agent projections, i.e. the rescaled first projections. Also the further, non-contrast-agent projections may be used for reconstructing the image.

The angular range over which the projection data are acquired for each set (i.e. each step of the step-and-shoot acquisition) may be any range suitable for reconstructing the object of interest, i.e., for instance the heart. Specifically, the angular range may be a super-short-scan where the radiation source travels along an angular range such that for each point of the object of interest the source is seen over 180°, it may be a classical short scan, where the radiation source moves over 180° plus the fan-angle of the computed tomography system, it may be a full scan, where the source travels over 360°, et cetera. Thus, the angular range may be a super short scan range or any larger range.

Although in above described embodiments the decomposition unit is adapted to use certain decomposition techniques for decomposing the spectral projections into first projections being indicative of the contrast agent within the subject and second projections not being indicative of the contrast agent within the subject, in other embodiments other decomposition techniques may be used for decomposing the spectral projections into first and second projections. Moreover, although in above described embodiments certain similarity measures have been used, in other embodiments other similarity measures may be used which allow for a comparison of the intensities of the first images in the overlapping regions.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the decomposition of the spectral projections, the scaling procedures, the reconstruction procedures, et cetera performed by one or several units or devices can be performed by any other number of units or devices. These procedures and/or the control of the computed tomography system in accordance with the computed tomography method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a computed tomography system. Several sets of spectral projections, which correspond to different positions of a radiation source along a rotation axis, are decomposed into first projections being indicative of a contrast agent and second projections being not indicative of the contrast agent. An image is generated by a) determining for each first projection a contrast value being indicative of a total amount of contrast agent and scaling the first projections such that for different first projections of a same set the same contrast value is determined, and reconstructing an image based on the scaled first projections, and/or b) reconstructing for the different sets first images, scaling the first images such that they have a same intensity in overlap regions and combining the scaled first images. Thus, different contrast agent amounts can be balanced, thereby allowing for an improved image quality.

The invention claimed is:
1. A computed tomography system for generating an image of a subject comprising a contrast agent, the computed tomography system comprising:
   a projections providing unit for providing several sets of spectral projections of the subject, wherein the several sets of projections have been acquired by detecting radiation, which has been emitted by a radiation source and which has traversed the subject, on a detection surface of a detector, while the radiation source and the subject have rotated relative to each other around a rotation axis, wherein different sets of spectral projections correspond to different positions of the radiation source along the rotation axis,
   a decomposition unit for decomposing the spectral projections into first projections being indicative of the contrast agent within the subject and second projections not being indicative of the contrast agent within the subject, an image generation unit for generating the image by reconstructing for the different sets first images based on the respective first projections, wherein the first images of the different sets partly overlap in overlap regions, scaling the first images of the different sets such that overlapping first images of the different sets have a same intensity in the respective overlap region with respect to a predefined similarity measure and combining the scaled first images for generating the image.

2. A computed tomography system for generating an image of a subject comprising a contrast agent according to claim 1, the computed tomography system comprising:

a projections providing unit for providing several sets of spectral projections of the subject, wherein the several sets of projections have been acquired by detecting radiation, which has been emitted by a radiation source and which has traversed the subject, on a detection surface of a detector, while the radiation source and the subject have rotated relative to each other around a rotation axis, wherein different sets of spectral projections correspond to different positions of the radiation source along the rotation axis, a decomposition unit for decomposing the spectral projections into first projections being indicative of the contrast agent within the subject and second projections not being indicative of the contrast agent within the subject, an image generation unit for generating the image by (a) determining for each first projection a contrast value being indicative of a total amount of contrast agent based on projection values of the respective first projection acquired within a respective region of interest on the detection surface and scaling the first projections such that for different first projections of a same set the same contrast value is determined, and reconstructing an image based on the scaled first projections and (b) reconstructing for the different sets first images based on the respective first projections, wherein the first images of the different sets partly overlap in overlap regions, scaling the first images of the different sets such that overlapping first images of the different sets have a same intensity in the respective overlap region with respect to a predefined similarity measure and combining the scaled first images for generating the image.

3. The computed tomography system as defined in claim 1, wherein the image generation unit is adapted to reconstruct the image based on the scaled first projections and the second projections.

4. The computed tomography system as defined in claim 1, wherein the image generation unit is adapted to reconstruct second images based on the respective second projections and to combine the scaled first images with the second images for generating the image.

5. The computed tomography system as defined in claim 1, wherein the subject is a living being and the provided sets of spectral projections are cardiac gated.

6. The computed tomography system as defined in claim 5, wherein the provided sets of spectral projections are prospective cardiac gated.

7. The computed tomography system as defined in claim 1, wherein the predefined similarity measure depends on an average of the intensity values of the respective first image in the respective overlap region.

8. The computed tomography system as defined in claim 1, wherein the region of interest on the detection surface is the entire detection surface.

9. The computed tomography system as defined in claim 1, wherein the respective region of interest on the detection surface corresponds to a virtual projection of a predefined object of interest within the subject on the detection surface.

10. The computed tomography system as defined in claim 9, wherein the projections providing unit is adapted to provide the respective acquisition geometry used for acquiring the respective projection and wherein the image generation unit is adapted to provide an object of interest image showing the object of interest within the subject and to determine the respective region of interest on the detection surface by virtually projecting the object of interest onto the detection surface under consideration of the provided respective acquisition geometry and the provided object of interest image.

11. The computed tomography system as defined in claim 1, wherein the image generation unit is adapted to parallel rebin the first projections before using the first projections for reconstruction.

12. A computed tomography method for generating an image of a subject comprising a contrast agent, the computed tomography method comprising:

providing several sets of spectral projections of the subject by a projections providing unit, wherein the several sets of projections have been acquired by detecting radiation, which has been emitted by a radiation source and which has traversed the subject, on a detection surface of a detector, while the radiation source and the subject have rotated relative to each other around a rotation axis, decomposing the spectral projections into first projections being indicative of the contrast agent within the subject and second projections being not indicative of the contrast agent within the subject by a decomposition unit, generating the image by an image generation unit by reconstructing for the different sets first images based on the respective first projections, wherein the first images of the different sets partly overlap in overlap regions, scaling the first images of the different sets such that overlapping first images of the different sets have a same intensity in the respective overlap region with respect to a predefined similarity measure and combining the scaled first images for generating the image.

13. A computed tomography method for generating an image of a subject comprising a contrast agent, the computed tomography method comprising:

providing several sets of spectral projections of the subject by a projections providing unit, wherein the several sets of projections have been acquired by detecting radiation, which has been emitted by a radiation source and which has traversed the subject, on a detection surface of a detector, while the radiation source and the subject have rotated relative to each other around a rotation axis, wherein different sets of spectral projections correspond to different positions of the radiation source along the rotation axis, decomposing the spectral projections into first projections being indicative of the contrast agent within the subject and second projections being not indicative of the contrast agent within the subject by a decomposition unit, generating the image by an image generation unit by (a) determining for each first projection a contrast value being indicative of a total amount of contrast agent based on projection values of the respective first projection acquired within a respective region of interest on the detection surface, scaling the first projections such that for different first projections of a same set the same contrast value is determined and reconstructing the image based on scaled first projections and the second projections and (b) reconstructing for the different sets first images based on the respective first projections and second images based on the respective second projections, wherein the first images of the different sets partly overlap in overlap regions, scaling the first images of the different sets such that overlapping first images of the different sets have a same intensity in the respective overlap region with respect to a predefined similarity measure and combining the scaled images for generating the image.

14. A computed tomography method for generating an image of a subject comprising a contrast agent, the computed tomography method comprising:

providing several sets of spectral projections of the subject by a projections providing unit, wherein the several sets of projections have been acquired by detecting radiation, which has been emitted by a radiation source and which has traversed the subject, on a detection surface of a detector, while the radiation source and the subject have rotated relative to each other around a rotation axis, wherein different sets of spectral projections correspond to different positions of the radiation source along the rotation axis, decomposing the spectral projections into first projections being indicative of the contrast agent within the subject and second projections being not indicative of the contrast agent within the subject by a decomposition unit, generating the image by an image generation unit by (b) reconstructing for the different sets first images based on the respective first projections and second images based on the respective second projections, wherein the first images of the different sets partly overlap in overlap regions, scaling the first images of the different sets such that overlapping first images of the different sets have a same intensity in the respective overlap region with respect to a predefined similarity measure and combining the scaled images for generating the image.

* * * * *